(12) United States Patent
Pursiheimo et al.

(10) Patent No.: US 11,486,003 B2
(45) Date of Patent: Nov. 1, 2022

(54) HIGHLY SENSITIVE METHODS FOR ACCURATE PARALLEL QUANTIFICATION OF NUCLEIC ACIDS

(71) Applicant: Genomill Health Oy, Turku (FI)

(72) Inventors: Juha-Pekka Pursiheimo, Paimio (FI); Tatu Hirvonen, Turku (FI); Manu Tamminen, Turku (FI); Anttoni Korkiakoski, Littoinen (FI)

(73) Assignee: Genomill Health Oy, Turku (FI)

( * ) Notice: Subject to any disclaimer, the term of this patent is extended or adjusted under 35 U.S.C. 154(b) by 0 days.

(21) Appl. No.: 17/685,964

(22) Filed: Mar. 3, 2022

(65) Prior Publication Data
US 2022/0298569 A1   Sep. 22, 2022

(30) Foreign Application Priority Data

Mar. 18, 2021 (EP) .................................. 21163300
Jan. 21, 2022 (EP) .................................. 22152617

(51) Int. Cl.
*C12P 19/34* (2006.01)
*C12Q 1/6874* (2018.01)
(52) U.S. Cl.
CPC ................................. *C12Q 1/6874* (2013.01)
(58) Field of Classification Search
CPC .................................................. C12Q 1/6869
See application file for complete search history.

(56) References Cited

U.S. PATENT DOCUMENTS

2020/0040376 A1* 2/2020 Russel ................. C12Q 1/6853
2020/0224243 A1* 7/2020 Desai .................... C12Q 1/682

FOREIGN PATENT DOCUMENTS

| WO | 2016123154 A1 | 8/2016 |
| WO | 2018045181 A1 | 3/2018 |
| WO | 2018109206 A1 | 6/2018 |
| WO | 2019038372 A1 | 2/2019 |

OTHER PUBLICATIONS

European Patent Office, Extended European Search Report, Application No. 2116300.3, dated Jul. 28, 2021, 6 pages.
European Patent Office, Extended European Search Report, Application No. 22152617.1, dated Jul. 18, 2022, 5 pages.

\* cited by examiner

*Primary Examiner* — Kenneth R Horlick
(74) *Attorney, Agent, or Firm* — Ziegler IP Law Group, LLC

(57) ABSTRACT

The present disclosure relates to a next generation DNA sequencing method and use for accurate and massively parallel quantification of one or more nucleic acid targets, for example in large volumes of unpurified sample material. More particularly, the present disclosure is related to a method and a kit comprising probes for detecting and quantifying genetic targets in complex samples. The disclosed embodiments includes one or more target-specific nucleic acid probes per genetic target (left probe and right probe) and a bridge oligo or bridge oligo complex.

14 Claims, 6 Drawing Sheets

Specification includes a Sequence Listing.

SEQUENCE LISTING

<160> NUMBER OF SEQ ID NOS: 31

<210> SEQ ID NO 1
<211> LENGTH: 31
<212> TYPE: DNA
<213> ORGANISM: Artificial Sequence

```
<220> FEATURE:
<223> OTHER INFORMATION: random sequence

<400> SEQUENCE: 1
ggggcccgcc gtcgatcgga gccgttagga t                              31

<210> SEQ ID NO 2
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 2
ttaaggtgcc gtcgatcgga gccgacgtac g                              31

<210> SEQ ID NO 3
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 3
ttaaggtgcc gtcgatcgga gccgacgtac g                              31

<210> SEQ ID NO 4
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 4
tataatagag gtcgtgcagt cacgacccgg t                              31

<210> SEQ ID NO 5
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 5
accaggtgcc gtcgatcgga gccgacccgg t                              31

<210> SEQ ID NO 6
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 6
gggccgggag gtcgtgcagt cacgttagga t                              31

<210> SEQ ID NO 7
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 7
tccaggtgag tcgatccgtc acgtacgtac g                              31
```

<210> SEQ ID NO 8
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 8
aaaattttag cgtacgtcgt acgtttagga t                              31

<210> SEQ ID NO 9
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 9
tataatagag gtcgtgcagt cacgacccgg t                              31

<210> SEQ ID NO 10
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 10
aggaccttga gtcgatccgc acgtacccgg t                              31

<210> SEQ ID NO 11
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 11
agcgaccgag gtcgtgcagt cacgacgtac g                              31

<210> SEQ ID NO 12
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 12
tataatagag gtcgtgcagt cacgacccgg t                              31

<210> SEQ ID NO 13
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 13
ggaaaaagcc gtcgatcgga gccgttagga t                              31

<210> SEQ ID NO 14
<211> LENGTH: 31
<212> TYPE: DNA
<213> ORGANISM: Artificial Sequence
<220> FEATURE:
<223> OTHER INFORMATION: random sequence - just for illustration -continued

```
<400> SEQUENCE: 14
atatacagag gtcgtgcagt cacgttagga t                                      31

<210> SEQ ID NO 15
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 15
gagagccgag gtcgtgcagt cacgacccgg t                                      31

<210> SEQ ID NO 16
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 16
cgcacgcgag gtcgtgcagt cacgacgtac g                                      31

<210> SEQ ID NO 17
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 17
attacaagcc gtcgatcgga gccgacccgg t                                      31

<210> SEQ ID NO 18
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 18
tataatagag gtcgtgcagt cacgacccgg t                                      31

<210> SEQ ID NO 19
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 19
gggcaattag cgtacgtcgt acgtacgtac g                                      31

<210> SEQ ID NO 20
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 20
tatgcgagcc gtcgatcgga gccgacgtac g                                      31
```

```
<210> SEQ ID NO 21
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 21
aggaccttga gtcgatccgc acgtacccgg t                                  31

<210> SEQ ID NO 22
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 22
attacaagcc gtcgatcgga gccgacccgg t                                  31

<210> SEQ ID NO 23
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 23
gaagaattag cgtacgtcgt acgtttagga t                                  31

<210> SEQ ID NO 24
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 24
gggcaattag cgtacgtcgt acgtacgtac g                                  31

<210> SEQ ID NO 25
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 25
gggcaattag cgtacgtcgt acgtacgtac g                                  31

<210> SEQ ID NO 26
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 26
gagcacttag cgtacgtcgt acgtacccgg t                                  31

<210> SEQ ID NO 27
<211> LENGTH: 31
<212> TYPE: DNA
<213> ORGANISM: Artificial Sequence
<220> FEATURE:
<223> OTHER INFORMATION: random sequence - just for illustration
```

```
<400> SEQUENCE: 27 aaagggcga gtcgatccgc acgtttagga t                              31

<210> SEQ ID NO 28
<211> LENGTH: 31
<212> TYPE: DNA
<213> ORGANISM: Artificial Sequence
<220> FEATURE:
<223> OTHER INFORMATION: random sequence - just for illustration

<400> SEQUENCE: 28
agcgcgcgcc gtcgatcgga gccgttagga t                             31

<210> SEQ ID NO 29
<211> LENGTH: 40
<212> TYPE: DNA
<213> ORGANISM: Artificial Sequence
<220> FEATURE:
<223> OTHER INFORMATION: random sequence - just for illustration

<400> SEQUENCE: 29
cgacgacgac agaaccagat acacgacgta cgcacgacat                    40

<210> SEQ ID NO 30
<211> LENGTH: 59
<212> TYPE: DNA
<213> ORGANISM: Artificial Sequence
<220> FEATURE:
<223> OTHER INFORMATION: random sequence - just for illustration
<220> FEATURE:
<221> NAME/KEY: misc_feature
<222> LOCATION: (33)..(42)
<223> OTHER INFORMATION: n is a, c, g, or t

<400> SEQUENCE: 30
ggttctgtcg tcgtcggaca cgacgctccg ctnnnnnnnn nnagctgagc gtattcgat    59

<210> SEQ ID NO 31
<211> LENGTH: 68
<212> TYPE: DNA
<213> ORGANISM: Artificial Sequence
<220> FEATURE:
<223> OTHER INFORMATION: random sequence - just for illustration
<220> FEATURE:
<221> NAME/KEY: misc_feature
<222> LOCATION: (18)..(27)
<223> OTHER INFORMATION: n is a, c, g, or t

<400> SEQUENCE: 31
ctggatcgtc gtatgctnnn nnnnnnngat cgacccattg gagaagatga tgtcgtgcgg    60
tacgtcgt                                                             68
```

HIGHLY SENSITIVE METHODS FOR ACCURATE PARALLEL QUANTIFICATION OF NUCLEIC ACIDS

TECHNICAL FIELD

The present invention disclosure relates to improved next generation DNA sequencing methods for accurate and massively parallel quantification of one or more nucleic acid targets. More particularly, the disclosure is related to methods and kits comprising probes for detecting and quantifying genetic targets in complex DNA pools primarily used for genetic target and variant detection. The invention uses one or more target-specific nucleic acid probes per genetic target (left probe and right probe) and a bridge oligo or bridge oligo complex.

BACKGROUND

With the advancement in the technology to study genetic variation, detection of the same in plants and animals is not cumbersome. However, detecting and accurately quantifying genetic variations such as mutations, in particular in samples having weak signals is currently still cumbersome, laborious and expensive, despite decreased sequencing costs. Various problems can be expressed more accurately such as specificity in order to detect genetic signals against a consensus background, sensitivity in order to detect weak genetic signals, accuracy for accurate quantification of the detected signals, throughput number of targeted genetic targets per assay, cost per assay, scaling to determine the assay cost scale when assaying multiple samples in parallel and turn-over to determine how long is the time from sampling to the results.

Currently, the typical quantification methods for liquid biopsies and conceptually similar assays (such as antibiotic resistance gene detection) include quantitative PCR (qPCR), array qPCR, digital PCR, multiplex ligation-dependent probe Amplification (MLPA) or quantification from next-generation DNA sequencing data. While the quantification methods are robust and well-established methods, each of the method is associated with specific problems discussed in closer detail below:

Quantitative PCR: Quantitative PCR (qPCR), is a technique which includes the amplification of a targeted DNA molecule during the PCR, i.e. in real-time. Real-time PCR can be used quantitatively (quantitative real-time PCR), and semi-quantitatively, i.e. above/below a certain amount of DNA molecules (semi quantitative real-time PCR). Quantitative PCR (qPCR) is a gold standard of genetic target quantification. Currently, the laboratory cost of a qPCR reaction is approximately $2. However, counting in the considerable hands-on time (labour cost) for setting up the reaction, the need for standard curves, along with replicates for each quantified target, the real cost is in fact much higher. The amount of hands-on time scales steeply with an increasing number of samples since a separate quantification experiment is required for each genetic target.

Array PCR: PCR Arrays are the most reliable tools for analyzing the expression of a relevant pathway- or disease-focused panel of genes. Each 96-well plate, 384-well plate, or 100-well disc PCR Array includes SYBR Green-optimized primer assays for a thoroughly researched panel of focused panel of genes. A newer iteration of the qPCR technology is array qPCR which miniaturizes the individual qPCR reactions. Array PCR brings down the cost of an individual qPCR reaction and improves the scalability of the method to multiple targets and samples. However, the method is currently limited to profiling 384 targets from 12 samples (or conversely 12 targets from 384 samples) at a cost of thousands of dollars per chip plus a large capital cost of the read-out infrastructure. Profiling thousands of samples using the aforementioned setup, therefore, remains prohibitively expensive.

Digital PCR: Digital polymerase chain reaction (digital PCR, DigitalPCR, dPCR, or dePCR) is a method to provide absolute quantification of targets through droplet-microfluidics and fluorescent detection. The methodology is relatively cost-effective (one target per sample costs around $3), but the hands-on time for preparing, setting-up and running individual experiments for each target in each sample scales poorly to thousands of samples.

Multiplex Ligation-dependent Probe Amplification (MLPA) provides an approach to simplify the detection of multiple genetic targets in individual samples. However, MLPA provides only relative quantification of targets, and requires a separate detection experiment for each sample. More recently, a variant of MLPA introduces concepts from DNA barcoding. The concept permits a better quantitative resolution and sample multiplexing than the traditional MLPA workflow.

Next generation sequencing-based approaches: Next-generation sequencing (NGS), also known as high-throughput sequencing that makes sequence-based gene expression analysis a "digital" alternative to analog techniques. Target counting from next-generation DNA sequencing data is becoming increasingly attractive as the cost of DNA sequencing keeps decreasing, and is currently used for instance in NIPT screening. However, the current approach suffers from high sequencing library preparation costs and sequencing efforts that is wasted on sequencing non-relevant genetic targets. For instance, in cancer-related liquid biopsies, non-targeted approaches result in wastage of sequencing effort on oncologically non-relevant loci. In fetal diagnostics, non-targeted sampling of loci considerably limits the statistical options for interpreting the data. Guardant Health Inc provides more targeted sequencing approach, where an array of RNA capture probes enriches targets for next-generation DNA sequencing.

Akhras et al. (2007) PLoS ONE 2(2):e223 disclose a multiplex pathogen detection assay involving barcoded target-specific probes, target circularization and sequencing. Use of a bridging oligonucleotide to ligate the target-specific probes is also disclosed.

WO2018109206 describes methods for the detection of analytes in a sample using padlock probes and rolling circle amplification. The use of a bridging oligo is not described.

WO2019038372 describes a next-generation sequencing approach wherein target sequences of interest are selectively amplified by in vitro transcription from ligation complexes containing a promoter for T7 polymerase, followed by cDNA synthesis and sequencing. While this method allows accurate and parallel detection and quantification of many target sequences in a sample, more complex, large volume, dilute and/or impure samples remain challenging.

Therefore, in light of the foregoing discussion, there exists a need to overcome the aforementioned drawbacks such as, but not limited to, specificity, sensitivity, accuracy, throughput, cost, scaling and turn-over through an accurate and massively parallel quantification of nucleic acid targets.

SUMMARY OF THE INVENTION

The present invention provides a method for using next-generation sequencing for highly sensitive, scalable and accurate target quantification from large volume samples (up to tens of milliliters) and/or dilute and/or non-purified sample material. Furthermore, an RNA amplification step such as described in WO2019038372 is avoided, rendering the method more simple.

In a first main aspect, the invention relates to a method for the high-throughput detection of one or more target nucleotide sequence in a plurality of samples, the method comprising the steps of:

(i) providing for each target nucleotide sequence in each of the samples:
a first probe, a second probe and a bridge oligo or a plurality of oligonucleotides capable of annealing to each other to form a bridge oligo complex,
wherein the first probe comprises, starting from the 5' end of the molecule, a first bridge oligo-specific sequence, optionally a first sequence barcode, and a first target specific portion at the 3' end of first probe;
and wherein the second probe comprises, starting from the 5' end of the molecule, a second target specific portion, optionally a second sequence barcode, and a second bridge oligo-specific sequence at the 3' end of second probe;
and wherein the bridge oligo or bridge oligo complex contains sequences complementary to the first bridge oligo-specific sequence and the second bridge oligo-specific sequence in the first probe and the second probe, respectively, and optionally a third barcode;
and wherein at least one of the first sequence barcode or the second sequence barcode or the third barcode is present in the first probe or the second probe or the bridge oligo or bridge oligo complex, respectively;
and wherein at least one of the first probe or the second probe or the bridge oligo or bridge oligo complex comprises a recognition sequence for an endonuclease;
and wherein, optionally, at least one of the first probe or the second probe or the bridge oligo or bridge oligo complex comprises a first capture moiety,
(ii) contacting, for each of the one or more target nucleotide sequence, the first probe and the second probe with, preferably for each of the samples in a separate tube, the bridge oligo or plurality of oligonucleotides capable of forming a bridge oligo complex and allow self-annealing into a plurality of ligation complexes;
(iii) contacting nucleic acids present in each of the samples to be tested for the target nucleotide sequences with the ligation complexes;
(iv) allowing the first target specific portion and the second target specific portion of the respective first probe and the second probe to hybridize to essentially adjacent sections on the target sequence, thereby forming a hybridization complex;
(v) optionally, bringing the hybridization complex in contact with a solid support comprising a second capture moiety, allowing the first capture moiety and the second capture moiety to interact such that the hybridization complexes become linked to the solid support and separating the solid-support-linked hybridization complexes from components of the samples that are not linked to the solid-support;
(vi) ligating the probes in the hybridization complexes to provide ligated ligation complexes;
(vii) pooling the ligated ligation complexes from the plurality of samples;
(viii) amplifying nucleic acids from the one or more ligated ligation complexes using rolling circle amplification with a strand-displacing polymerase;
(ix) optionally subjecting the amplified one or more single-stranded concatemeric sequence obtained in step (viii) to annealing with a specific oligonucleotide containing a recognition sequence for an endonuclease wherein the oligonucleotide anneals with the recognition sequence specified in step (i) such that a recognition site for the endonuclease is obtained;
(x) optionally cleaving the single-stranded concatemeric sequence obtained in step (viii) or the annealed complexes obtained in step (ix) with said endonuclease;
(xi) subjecting the nucleic acid fragments obtained in step (x) or the concatemeric sequence obtained in step (viii) to high-throughput sequencing technology to determine the barcode sequence(s); and
(xii) identifying the presence and/or number of the target nucleotide sequence in the plurality of samples by determination of at least part of the first target specific portion and/or the second target specific portion, and/or at least part of the first barcode and/or the second barcode, and/or at least part of the third barcode,
wherein steps (vi) and (vii) may be performed in any order.

DETAILED DESCRIPTION OF THE INVENTION

Definitions

Figure 1:
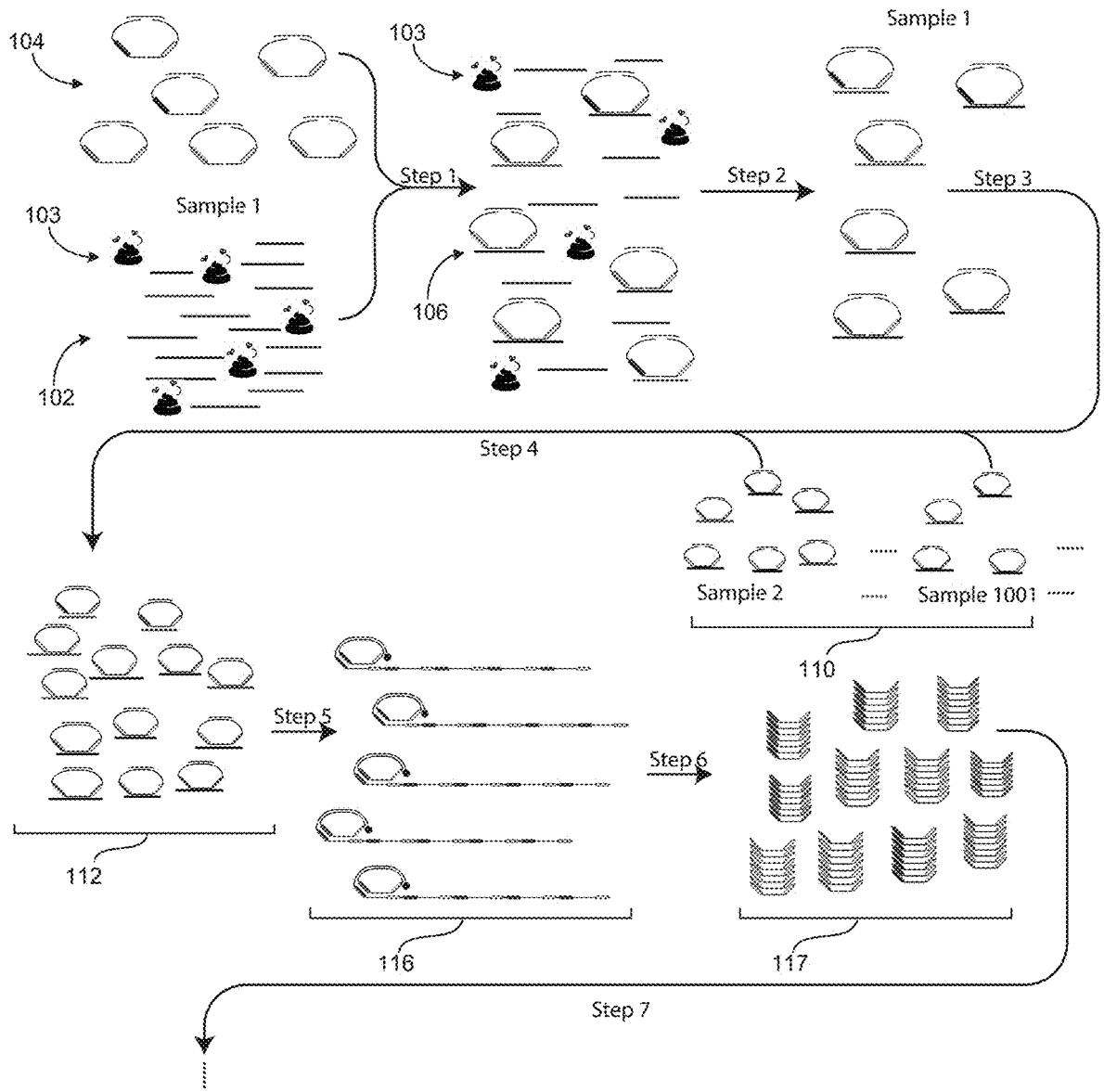
FIG. 1 illustrates a flow diagram of the Multiplexed Ligation Assay (MLA) according to an embodiment herein.

Target Nucleotide Sequence: The term target nucleotide sequence may be any nucleotide sequence of interest of which its detection is required. It will be understood that the term given refers to a sequence of contiguous nucleotides as well as to nucleic acid molecules with the complementary sequence. The target sequence in some embodiments is a nucleotide sequence that represents or is associated with a polymorphism.

Polymorphism: The term polymorphism refers to an occurrence of two or more genetically determined alternative sequences or alleles in a population. A polymorphic marker or site is the locus at which sequence divergence occurs. A polymorphic locus may be as small as one base pair.

Samples: The term samples is used herein for two or more samples which contain two or more target sequences.

Samples as provided in a method according to the invention may have been prepared in order to extract at least the target nucleic acids and make those accessible to the probes as used in the invention. In particular, in some embodiments, the samples each comprise at least two different target sequences, preferably at least 100, more preferably at least 250, more preferably at least 500, most preferably at least 2000, or more. The term samples may refer to but is not limited to two or more samples obtained from a human/animal body, including urine, biopsies, saliva and other secretions, exhaled moisture extracts, tissue, blood plasma (liquid biopsies), or two or more samples obtained from the environment, including water, wastewater, soil, plants, or two or more samples containing viruses or bacteria or the like. In one embodiment, the plurality of samples includes a blood sample, a saliva sample, a urine sample or a feces sample, a sample of another body fluid or an extract from body material, for example hair or skin flakes.

Probe: The term probe is a fragment of DNA or RNA of variable length (usually 50-1000 bases long, preferably 50-200 bases long) which can be used in DNA or RNA samples to detect the presence of nucleotide sequences (the DNA or RNA target) that are complementary to the sequence in the probe. The sections of the oligonucleotide probes that are complementary to the target sequence are designed such that for each target sequence in a sample, a pair of a left and a right probe is provided, whereby the probes each contain a section at their extreme end that is complementary to a part of the target sequence. Furthermore, the present disclosure describes a bridge oligo or bridge oligo complex that is used for joining the left probe and the right probe.

Universal: The term universal when used to describe an amplification procedure refers to a sequence that enables the use of a single primer or set of primers for a plurality of amplification reactions. The use of such primers greatly simplifies multiplexing in that only two primers are needed to amplify a plurality of selected nucleic acid sequences. The term universal when used to describe a priming site is a site to which a universal primer will hybridize. It should also be noted that "sets" of universal priming sequences/primers may be used.

Hybridization: The term hybridization (or hybridisation) describes the process of deoxyribonucleic acid (DNA) or ribonucleic acid (RNA) molecules annealing to complementary DNA or RNA. DNA or RNA replication and transcription of DNA into RNA both rely on nucleotide hybridization.

Ligation: The term ligation is the joining of two nucleic acid fragments through the action of an enzyme. DNA ligases are enzymes capable of catalyzing the formation of a phosphodiester bond between (the ends of) two polynucleotide strands bound at adjacent sites on a complementary strand. In one embodiment, ligation can also be performed chemically, in particular if both adjacent ends of the polynucleotides are modified to allow chemical ligation.

Amplification: The term amplification as used herein denotes the use of a DNA polymerase to increase the concentration of a particular nucleotide sequence within a mixture of nucleotide sequences. "PCR" or "Polymerase Chain Reaction" is a rapid procedure for in vitro enzymatic amplification of a specific DNA/RNA segment. The DNA/RNA to be amplified may be denatured by heating the sample. The term primer is a short strand of RNA or DNA (generally about 18-22 bases) that serves as a starting point for DNA synthesis. It is required for DNA replication because the enzymes that catalyze this process, DNA polymerases, can only add new nucleotides to an existing strand of DNA.

Polymerase: A polymerase is an enzyme that synthesizes long chains or polymers of nucleic acids. DNA polymerase and RNA polymerase are used to assemble DNA and RNA molecules, respectively, by copying a DNA or RNA template strand using base-pairing interactions.

High throughput: The term high throughput denotes the ability to simultaneously process and screen a large number of DNA samples; as well as to simultaneously screen large numbers of different genetic loci within a single DNA sample. High-throughput sequencing or screening, often abbreviated as HTS is a method for scientific experimentation especially relevant to effectively screen large amounts of samples simultaneously.

Endonuclease: An endonuclease is an enzyme that cleaves DNA double or single strand at a random or specified location.

As described above, the disclosure relates to a method for the high-throughput detection of target nucleotide sequence detection in a very large number of samples by leveraging ligation-dependent assays. The disclosure provides a method for determining the sequences of genetic targets in complex nucleic acid pools using techniques permitted by next generation sequencing. The disclosure also provides a method to profile multiple genetic targets in a number of samples, preferably a very large number of samples, by leveraging ligation-dependent assays. The disclosure provides a method for the multiplex ligation-dependent probe amplification enabling querying different target nucleic acids in a plurality of samples. The methods of the present invention allow the sequencing of the one or more target nucleotide sequence in a plurality of samples providing a plurality of different probe sets for different target nucleic acids. Unique sequence identifiers are used for the identification of the genetic targets and absolute quantification of individual samples from the sample pool when processing the sequencing data.

In a first main aspect, the invention relates to a method for the high-throughput detection of one or more target nucleotide sequence in a plurality of samples, the method comprising the steps of:
 (i) providing for each target nucleotide sequence in each of the samples:
  a first probe, a second probe and a bridge oligo or a plurality of oligonucleotides capable of annealing to each other to form a bridge oligo complex,
  wherein the first probe comprises, starting from the 5' end of the molecule, a first bridge oligo-specific sequence, optionally a first sequence barcode, and a first target specific portion at the 3' end of first probe;
  and wherein the second probe comprises, starting from the 5' end of the molecule, a second target specific portion, optionally a second sequence barcode, and a second bridge oligo-specific sequence at the 3' end of second probe;
  and wherein the bridge oligo or bridge oligo complex contains sequences complementary to the first bridge oligo-specific sequence and the second bridge oligo-specific sequence in the first probe and the second probe, respectively, and optionally a third barcode;
  and wherein at least one of the first sequence barcode or the second sequence barcode or the third barcode is present in the first probe or the second probe or the bridge oligo or bridge oligo complex, respectively;
  and wherein at least one of the first probe or the second probe or the bridge oligo or bridge oligo complex comprises a recognition sequence for an endonuclease;

and wherein, optionally, at least one of the first probe or the second probe or the bridge oligo or bridge oligo complex comprises a first capture moiety, (ii) contacting, for each of the one or more target nucleotide sequence, the first probe and the second probe with, preferably for each of the samples in a separate tube, the bridge oligo or plurality of oligonucleotides capable of forming a bridge oligo complex and allow self-annealing into a plurality of ligation complexes;

(iii) contacting nucleic acids present in each of the samples to be tested for the target nucleotide sequences with the ligation complexes;

(iv) allowing the first target specific portion and the second target specific portion of the respective first probe and the second probe to hybridize to essentially adjacent sections on the target sequence, thereby forming a hybridization complex;

(v) optionally, bringing the hybridization complex in contact with a solid support comprising a second capture moiety, allowing the first capture moiety and the second capture moiety to interact such that the hybridization complexes become linked to the solid support and separating the solid-support-linked hybridization complexes from components of the samples that are not linked to the solid-support;

(vi) ligating the probes in the hybridization complexes to provide ligated ligation complexes;

(vii) pooling the ligated ligation complexes from the plurality of samples;

(viii) amplifying nucleic acids from the one or more ligated ligation complexes using rolling circle amplification with a strand-displacing polymerase;

(ix) optionally subjecting the amplified one or more single-stranded concatemeric sequence obtained in step (viii) to annealing with a specific oligonucleotide containing a recognition sequence for an endonuclease wherein the oligonucleotide anneals with the recognition sequence specified in step (i) such that a recognition site for the endonuclease is obtained;

(x) optionally cleaving the single-stranded concatemeric sequence obtained in step (viii) or the annealed complexes obtained in step (ix) with said endonuclease;

(xi) subjecting the nucleic acid fragments obtained in step (x) or the concatemeric sequence obtained in step (viii) to high-throughput sequencing technology to determine the barcode sequence(s); and (xii) identifying the presence and/or number of the target nucleotide sequence in the plurality of samples by determination of at least part of the first target specific portion and/or the second target specific portion, and/or at least part of the first barcode and/or the second barcode, and/or at least part of the third barcode, wherein steps (vi) and (vii) may be performed in any order.

FIG. 1 provides a non-limiting illustration of an embodiment of the method of the invention.

The methods of the present invention utilize three nucleic acid probes, out of which two target-specific nucleic acid probes (left probe and right probe) are specific for a genetic target and one nucleic acid probe typically is universal (bridge oligo or bridge oligo complex). The left and right probe hybridize to the bridge probe or bridge oligo complex, forming a ligation complex. The ligation complexes (containing one or more barcode sequences) having target identification sites on the sample DNA or RNA are allowed to hybridize against complementary target sequences of the query sample. After hybridization, the left and right probe are ligated chemically or enzymatically by a DNA ligase to form ligated ligation complex. In the present invention, a plurality of such ligated ligation complexes will form during the sample analysis in the plurality of samples to be analyzed.

In an embodiment, "plurality of samples" may refer to, but not limited to, two or more samples obtained from the human or animal body, including biopsies, saliva and other secretions, exhaled moisture extracts, tissue, blood plasma (liquid biopsies), two or more samples obtained from environment, including water, wastewater, soil, plants, or two or more samples containing viruses or bacteria or the like. In one embodiment, the sample is used without any prior purification or concentration of nucleic acid. In another embodiment, the sample may be pre-treated, for instance lysing cells to expose nucleic acid.

The target sequence may include any nucleotide sequence of interest against which the detection is required. The target nucleotide sequence of the disclosure may be obtained from, but not limited to, a fraction of DNA in the patient's blood or a fraction of DNA in maternal blood. A fraction of the DNA in the patient's blood may be obtained from apoptotic/necrotic cancer cells or a fraction of DNA in maternal blood from fetal and/or maternal origin. Further, the results of analysis are used to, for instance, assess the risk of an individual to a given type of cancer, to determine the efficacy of a given treatment against a given cancer, the development of a drug-resistance-related mutations in a tumor, or the risk of a fetus carrying genetic disorders such as common trisomies Down, Patau and Edwards syndromes. In certain embodiments, the method comprises providing, for each target nucleotide sequence, a plurality of different probe sets.

As used herein, the term probe sets includes a first probe, a second probe and a bridge oligo or bridge oligo complex.

In certain embodiments, the first probe includes, starting from the 5' end of the molecule, optionally a 5' phosphate, a first bridge oligo-specific sequence, optionally a first universal sequence, optionally a first sequence barcode, and a first target specific portion at its 3' end. In certain embodiments, the second probe includes, starting from 5' end of the molecule, optionally a 5' phosphate, a second target specific portion, optionally a second sequence barcode, optionally a second universal sequence, and a second bridge oligo-specific sequence at its 3' end.

In a preferred embodiment, either the first probe or the second probe contains at least one of the first sequence barcode or the second sequence barcode. The first sequence barcode or the second sequence barcode, or both, may be random sequences or may contain target nucleotide sequence identifier sequences, sample identifier sequences and/or molecular barcodes for target enumeration.

In preferred embodiments, the bridge oligo or bridge oligo complex contains sequences complementary to the first and second bridge oligo-specific sequences in the first and second probe, respectively, optionally a universal sequence, and/or or may contain a third barcode which may be a random sequence or may contain a sample or sequence identifier sequence. In this respect, third barcode does not necessarily mean that there are already a first and a second barcode present. As described earlier, at least one barcode should be present in the ligated ligation complex, that enables to uniquely define the complex within all ligation complexes in all samples tested.

Furthermore, at least one of the first probe or the second probe or the bridge oligo or bridge oligo complex comprises a recognition sequence for an endonuclease. The recognition sequence is required for the cleavage of the concatemeric sequence in step (x). In one embodiment, the recognition sequence is a recognition sequence for a restriction endonuclease such as EcoRI. In another embodiment, the recognition sequence is a recognition sequence for a homing endonuclease such as I-CeuI. In another embodiment the recognition sequence is a recognition sequence for a guided DNAaseI or CRISPR-Cas-like cleavage system.

Optionally, at least one of the first probe or the second probe or the bridge oligo or bridge oligo complex comprises a first capture moiety. A first capture moiety, when used herein, refers to a moiety, such as a chemical group, which allows the probe, ligation complex or hybridization complex to be captured by, i.e. bound to, a second capture moiety which is linked to a solid support. Any suitable capture moiety known in the art may be used for this purpose. A well-known suitable example is the capture of biotinylated molecules using streptavidin-coated magnetic beads. Thus, in one embodiment, the first capture moiety is a biotin moiety, which can interact with a streptavidin or avidin moiety (the second capture moiety) linked to a solid support, such as a magnetic bead. Other options include biotin derivatives such as dual-biotin, desthiobiotin or photocleavable biotin which can be used for conjugation with streptavidin/avidin. Further options include the use of thiol and acrydite groups for acrydite/acrylamide conjugation, alkyne and azide groups for click chemistry and digoxigenin for anti-digoxigenin antibody conjugation. The conjugation partners can be provided on any solid surfaces such as beads (magnetic or otherwise) or solid supports.

Figure 3:
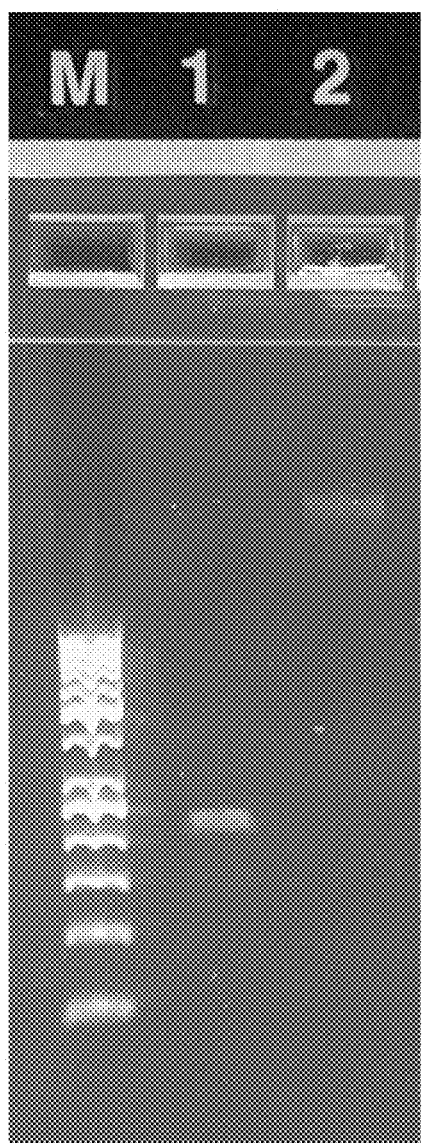
FIG. 3 illustrates the RCA products from the workflow before (lane 2) and after (lane 1) digestion by a restriction endonuclease.

The first target specific portion, the second target specific portion, the first bridge oligo-specific sequences, and/or the second bridge oligo-specific sequences, preferably contain independently from one another at least one chemically modified nucleotide to increase probe binding. The chemical modifications that increase probe binding include, but are not limited to, ribonucleic acids, peptide nucleic acids, and locked nucleic acids (e.g. as illustrated in FIG. 3 of WO2019038372, incorporated herein by reference). In one embodiment, the bridging portion of the first probe or the second probe, or both, comprise(s) chemically modified bases to permit improved binding to the bridge oligo or bridge oligo complex. In another embodiment, the first target specific portion, the second target specific portion, the first bridge oligo-specific sequences, and/or the second bridge oligo-specific sequences, contain independently from one another, one or more chemically modified nucleotides. In certain embodiments, chemical modifications permit chemical ligation of adjacent probes. In some embodiments, the aforementioned probes bind to completely adjacent genetic loci or up to 500 base pairs apart, for example up to 200 base pairs apart, such as up to 50 base pairs apart, preferably up to 40 base pairs apart, more preferably up to 30 base pairs apart, more preferably up to 20 base pairs apart, more preferably up to 10 base pairs apart, most preferably up to 5 base pairs apart.

In some embodiments, the first probe or the second probe or the bridge oligo or bridge oligo complex may include adapter sequences for a DNA sequencing platform such as (but not limited to) Illumina. These adapter sequences permit the resulting sequencing libraries to bind to the detection parts of the sequencing devices such as Illumina flow cells.

Furthermore, in some embodiments, the bridge oligo or bridge oligo complex comprises:
(i) one to five 3' protruding bases (i.e. additional bases which do not form double helix with the second probe), and/or
(ii) 3' phosphate, and/or
(iii) one or more phosphorothioate modifications within three positions from the 3' end.

Before contacting the probes with the sample comprising the target sequences, the first probe and the second probe are brought in contact with the bridge oligo or plurality of oligonucleotides capable of forming a bridge oligo complex, preferably for each of the samples in a separate tube, and self-annealing into ligation complexes is allowed (step (ii)). In an embodiment wherein the bridge is not one oligo, but a plurality of oligonucleotides, such as three or five oligonucleotides, capable of annealing to each other to form a bridge oligo complex (illustrated herein in FIG. 2C), the plurality of oligonucleotides may be pre-annealed before annealing with the first and second probes or all annealing steps may be done at once.

Preferably each ligation complex is unique for the combination of the first target specific sequence, the second target specific sequence and one or more barcode sequences. This enables enumeration of the target sequences after amplification and analysis of the results.

Thereafter, one or more target nucleotide sequences in the plurality of samples is brought into contact with the plurality of ligation complexes (step (iii)). The first target specific portion of the respective first probe and the second target specific portion of the respective first probe and the second probe hybridize to essentially adjacent sections on the target sequence, thereby forming a hybridization complex (step (iv)). In some embodiments, the sample has a volume of more than 100 microliters, e.g. more than 1 ml. In a further embodiment, the sample has a nucleic acid concentration below 5 pmol, such as below 1 pmol, for example below 200 fmol. In one embodiment, the plurality of samples includes one or more blood samples, one or more saliva samples, one or more urine samples or one or more feces samples.

Subsequently, in some embodiments, if at least one of the first probe or the second probe or the bridge oligo or bridge oligo complex comprises a first capture moiety, the hybridization complex(es) are brought in contact with a solid support comprising a second capture moiety and the first capture moiety and the second capture moiety are allowed to interact such that the hybridization complex(es) become linked to the solid support (optional step (v)). Thereafter, the solid-support-linked hybridization complexes are separated from components of the samples that are not linked to the solid-support. If the solid supports are magnetic beads, the beads may be immobilized using a magnet and the remaining liquid sample may be removed. Optionally, a wash step is performed before proceeding.

Step (v) results in a purification and enrichment for nucleic acid, allowing improved results in particular for highly impure samples. In one embodiment, the method of the invention does not comprise a step of enriching for nucleic acids prior to step (v). Thus, in one embodiment, the method does not contain prior to step (vi) a step wherein nucleic acids in the original sample are concentrated more than 2-fold, more than 10-fold, or more than 100-fold. In another embodiment, the method of the invention does not include a purification step subsequent to the ligation in step (vi).

Subsequently, ligation of the probes in the formed hybridized complexes is carried out either enzymatically or chemically to provide ligated ligation complexes (step (vi)). Optionally as a part of step (vi), a gap between the first probe and the second probe, if present, may be filled by introducing a polymerase and one or more nucleotides. The polymerase adds nucleotides (a) complimentary to the universal bridge oligo sequence and/or (b) complimentary to the barcode sequence and thereby fills in the two gaps between the first probe and the second probe resulting in ligated the left and the right probe and inclusion of the universal sequence and/or third barcode sequence into the bridge complementary strand. The bridge oligo or bridge oligo complex is extended from the 5' site or the 3' site complimentary to the ligated probes such that the target sequence identifier sequence present in the first probe or second probe is integrated into the bridge oligo or bridge oligo complex. Preferably, a polymerase is used that does not break up double stranded DNA, such as for instance a Taq polymerase, in order not to interfere with the ligation of the first to the second probe when both are annealed to the target sequence.

The ligated ligation complexes are then pooled from one or more target samples (step (vii)). Steps (vi) and (vii) may be performed in the specified order or alternatively in reverse order.

Next, nucleic acids are amplified from the one or more ligated ligation complexes (step (viii)). Amplification is performed using rolling circle amplification with a strand-displacing polymerase, such as phi29 polymerase (UniProtKB-P03680; DPOL_BPPH2) or a Bst polymerase (P52026; DPO1_GEOSE). In the following step (ix), the amplified one or more single-stranded concatemeric sequences obtained in step (viii) are optionally subjected to annealing with a specific oligonucleotide containing a recognition sequence for an endonuclease wherein said oligonucleotide anneals with said recognition sequence specified in step (i) such that a recognition site for the endonuclease is obtained. The specific oligonucleotide containing the recognition sequence will typically contain some additional specific sequences around the recognition sequences in order to allow formation of stable double-helix for cleavage.

Subsequently, the single-stranded concatemeric sequence obtained in step (viii) or the annealed complexes obtained in step (ix) are optionally cleaved with said endonuclease (step (x)), resulting in an NGS library.

Optionally, after amplification, the solid supports, if present, are removed and the supernatant is used for subsequent processing. For example, if the solid supports are magnetic particles, these may be removed using a magnet. In some other embodiments of the method of the invention, the interaction between the first capture moiety and the second capture moiety is disrupted immediately after step (vi), after step (vii) or after step (viii). For example, if the first capture moiety is biotin and the second capture moiety is streptavidin, the interaction can be disrupted by adding excess soluble biotin. If the streptavidin is bound to magnetic particles, it can subsequently be removed using a magnet.

Furthermore, optionally, a PCR amplification is performed between step (x) and step (xi) using primers which bind to universal parts of the first and second probes, wherein said primers optionally include adapter sequences for the subsequent sequencing in step (xi).

The identification of the presence and/or number of the target nucleotide sequence in the plurality of samples may be performed by determination of at least part of the first and/or second target specific portion, at least part of the first and/or second barcode, and/or at least part of the third barcode by high-throughput sequencing technology (steps (xi) and (xii)), for example using a next-generation sequencing platform including without limiting, Illumina iSeq, MiSeq, HiSeq, NextSeq or NovaSeq. Preferably, the genetic target enumeration is permitted by counting the number of molecular barcodes per target and per sample. The samples are separated (de-convoluted) from the sequence data and the sequence targets quantified in silico after the DNA sequencing.

In a preferred embodiment, the molecules are further amplified with a first primer and a second primer to provide an amplification product. Preferably a universal first primer and a universal second primer are used, reverse complementary to a first or second universal sequence present in the ligated complexes.

The advantages of the present invention include, but are not limited to quantification assay with low cost, high simplicity, high specificity, high sensitivity, high accuracy, high throughput, high scalability and high turn-over in comparison to traditional nucleic acid sequencing technologies. Another aspect of the present invention is that the methods of the present invention allow accurate and massively parallel quantification of plurality of nucleic acid targets in multiple samples including human and animal populations, and including large volumes of unpurified sample material. As mentioned, in a preferred embodiment, the sample, such as a urine sample, is used without any prior purification or concentration of nucleic acid. In another embodiment, the sample may be pre-treated, for instance lysing cells to expose nucleic acid. One particular advantage of the invention is to enable the detection and amplification of target sequence of interest using unique probe designs, i.e., probe triplet. The probes are designed with specially situated modified nucleotides that improve annealing and binding efficiency. Improvement in binding properties leads to higher assay specificity, sensitivity and accuracy. The methods of the present invention are likewise applicable for studying genetic variants and find application in diagnosis and prognosis, including but not limited to genotype the sample(s) for one or more sequences and/or polymorphisms, such as SNPs and/or indels, cancer diagnostics or fetal chromosomal disorders from maternal blood. In a preferred embodiment, for two or more samples or for two or more locus/allele combinations, barcode sequences are used to genotype the samples for one or more sequences and/or polymorphisms, such as SNPs and/or indels.

In another aspect, the invention provides a kit of parts comprising a plurality of containers, wherein at least one container comprises one or more sets of first probe and second probe, and at least one container comprises one or more bridge oligos or a plurality of oligonucleotides capable of annealing to each other to form a bridge oligo complex, wherein the first probe comprises, starting from the 5' end of the molecule, a first bridge oligo-specific sequence, optionally a first sequence barcode, and a first target specific portion at 3' end of first probe;

wherein the second probe comprises, starting from the 5' end of the molecule, a second target specific portion, optionally a second sequence barcode, and a second bridge oligo-specific sequence at 3' end of second probe;

wherein the bridge oligo or bridge oligo complex comprises sequences complementary to the first and second bridge oligo-specific sequences in the first and second probe, respectively, and optionally a third barcode;

wherein at least one of the first sequence barcode or the second sequence barcode or the third barcode is present in the first probe or the second probe or the bridge oligo or bridge oligo complex, respectively;

wherein at least one of the first probe or the second probe or the bridge oligo or bridge oligo complex comprises a recognition sequence for an endonuclease;

and wherein the kit of parts further comprises an oligonucleotide capable of annealing with said recognition sequence such that a recognition site for said endonuclease is obtained.

Preferably, the 3' end of the first probes or the 5' end of the second probes, or both, are modified to permit chemical ligation of the first probes to the second probes.

Preferably, the bridge oligo or bridge oligo complex comprises one or more chemically modified nucleotides in the sequence complementary to a sequence of the first probe or in the sequence complementary to a sequence of the second probe, or both.

Preferably, the 3' end of the first probe or the 5' end of the second probe, or both, are modified to permit chemical ligation of the first probe to the second probe.

Preferably, the bridging portion of the first probe or the second probe, or both, comprise(s) chemically modified bases to permit improved binding to the bridge oligo or bridge oligo complex.

In one particular embodiment, at least one container comprising the set of first and second probe and at least one container comprising the bridge oligo or a plurality of oligonucleotides capable of annealing to each other to form a bridge oligo complex, are one and the same container. In such case, the three probes may be pre-annealed and have formed a ligated complex.

One particular advantage of the invention is to enable the detection and amplification of target sequence of interest using unique probe designs i.e. probe triplet. The probes are designed with improved binding properties lead to higher assay specificity, sensitivity and accuracy. The present invention finds application in the area of molecular biology, evolutionary biology, metagenomics, genotyping and more specifically, but not limited to cancer diagnostics or fetal chromosomal disorders, including but not limited to genotype sample(s) for one or more sequences and/or polymorphisms, such as SNPs and/or indels.

In one particular preferred embodiment, the bridge oligo or bridge oligo complex comprises information to identify the sample and includes a unique barcode. In such case, the first and second probe is universally applicable to all samples (and only comprises information to identify the target). In one preferred embodiment, therefore, a method or a kit according to the invention is provided, wherein the bridge oligo or bridge oligo complex comprises a barcode that comprises a unique sequence that enables enumeration of the target sequences of each sample.

Furthermore, the invention relates to:

Embodiment 1: A method for the high-throughput detection of one or more target nucleotide sequence in a plurality of samples, the method comprising the steps of:
(i) providing for each target nucleotide sequence in each of the samples:
a first probe, a second probe and a bridge oligo,
wherein the first probe comprises, starting from the 5' end of the molecule, a first bridge oligo-specific sequence, optionally a first sequence barcode, and a first target specific portion at the 3' end of first probe;
and wherein the second probe comprises, starting from the 5' end of the molecule, a second target specific portion, optionally a second sequence barcode, and a second bridge oligo-specific sequence at the 3' end of second probe;
and wherein the bridge oligo contains sequences complementary to the first bridge oligo-specific sequence and the second bridge oligo-specific sequence in the first probe and the second probe, respectively, and optionally a third barcode;
and wherein at least one of the first sequence barcode or the second sequence barcode or the third barcode is present in the first probe or the second probe or the bridge oligo, respectively;
and wherein at least one of the first probe or the second probe or the bridge oligo comprises a recognition sequence for an endonuclease;
and wherein, optionally, at least one of the first probe or the second probe or the bridge oligo comprises a first capture moiety,
(ii) contacting, for each of the one or more target nucleotide sequence, the first probe and the second probe with, preferably for each of the samples in a separate tube, the bridge oligo and allow self-annealing into a plurality of ligation complexes;
(iii) contacting nucleic acids present in each of the samples to be tested for the target nucleotide sequences with the ligation complexes;
(iv) allowing the first target specific portion and the second target specific portion of the respective first probe and the second probe to hybridize to essentially adjacent sections on the target sequence, thereby forming a hybridization complex;
(v) optionally, bringing the hybridization complex in contact with a solid support comprising a second capture moiety, allowing the first capture moiety and the second capture moiety to interact such that the hybridization complexes become linked to the solid support and separating the solid-support-linked hybridization complexes from components of the samples that are not linked to the solid-support;
(vi) ligating the probes in the hybridization complexes to provide ligated ligation complexes;
(vii) pooling the ligated ligation complexes from the plurality of samples;
(viii) amplifying nucleic acids from the one or more ligated ligation complexes using rolling circle amplification with a strand-displacing polymerase;
(ix) optionally subjecting the amplified one or more single-stranded concatemeric sequence obtained in step (viii) to annealing with a specific oligonucleotide containing a recognition sequence for an endonuclease wherein the oligonucleotide anneals with the recognition sequence specified in step (i) such that a recognition site for the endonuclease is obtained;
(x) cleaving the single-stranded concatemeric sequence obtained in step (viii) or the annealed complexes obtained in step (ix) with said endonuclease;
(xi) subjecting the nucleic acid fragments obtained in step (x) to high-throughput sequencing technology to determine the barcode sequence(s); and
(xii) identifying the presence and/or number of the target nucleotide sequence in the plurality of samples by determination of at least part of the first target specific portion and/or the second target specific portion, and/or at least part of the first barcode and/or the second barcode, and/or at least part of the third barcode,
wherein steps (vi) and (vii) may be performed in any order.

Embodiment 2: Method according to embodiment 1, wherein the plurality of samples includes a blood sample, a saliva sample, a urine sample or a feces sample.

Embodiment 3: Method according to embodiment 1 or 2, wherein at least one of the first probe or the second probe or the bridge oligo comprises a first capture moiety, wherein the method comprises step (v), and wherein the method does not comprise a step of enriching for nucleic acids prior to step (v).

Embodiment 4: Method according to any one of embodiments 1-3, wherein at least one of the first probe or the second probe or the bridge oligo comprises a first capture moiety, wherein the method comprises step (v), and wherein the first capture moiety is a biotin moiety and the second capture moiety is a streptavidin moiety or an avidin moiety.

Embodiment 5: Method according to any one of embodiments 1-4, wherein at least one of the first probe or the second probe or the bridge oligo comprises a first capture moiety, wherein the method comprises step (v), and wherein a wash step is performed between steps (v) and (vi).

Embodiment 6: Method according to any one of embodiments 1-5, wherein the bridge oligo comprises:
(i) one to five 3' protruding bases, and/or
(ii) 3' phosphate, and/or
(iii) one or more phosphorothioate modifications within three positions from the 3' end.

Embodiment 7: Method according to any one of embodiments 1-6, wherein the 3' end of the first probe or the 5' end of the second probe, or both, are modified to permit chemical ligation of the first probe to the second probe.

Embodiment 8: Method according to any one of embodiments 1-7, wherein the bridging portion of the first probe or the second probe, or both, comprise(s) chemically modified bases to permit improved binding to the bridge oligo.

Embodiment 9: Method according to any one of embodiments 1-8, wherein the first target specific portion, the second target specific portion, the first bridge oligo-specific sequences, and/or the second bridge oligo-specific sequences, contain independently from one another, one or more chemically modified nucleotide.

Embodiment 10: Method according to any one of embodiments 1-9, wherein step (viii) is performed using a phi29 polymerase or a Bst polymerase.

Embodiment 11: Method according to any one of claim 1-9, wherein a PCR amplification is performed between step (x) and step (xi) using primers which bind to universal parts of the first and second probes, wherein said primers optionally include adapters for subsequent sequencing in step (xi).

Embodiment 12: Method according to any one of embodiments 1-11, wherein genetic target enumeration is permitted by counting the number of molecular barcodes per target and per sample.

Embodiment 13: Method according to any one of embodiments 1-12, wherein for two or more samples or for two or more locus/allele combinations, barcode sequences are used to genotype the sample(s) for one or more sequences and/or polymorphisms, such as SNPs and/or indels.

Embodiment 14: Kit of parts comprising a plurality of containers,
wherein at least one container comprises one or more sets of first probe and second probe, and at least one container comprises one or more bridge oligos,
wherein the first probe comprises, starting from the 5' end of the molecule, a first bridge oligo-specific sequence, optionally a first sequence barcode, and a first target specific portion at 3' end of first probe;
wherein the second probe comprises, starting from the 5' end of the molecule, a second target specific portion, optionally a second sequence barcode, and a second bridge oligo-specific sequence at 3' end of second probe;
wherein the bridge oligo comprises sequences complementary to the first and second bridge oligo-specific sequences in the first and second probe, respectively, and optionally a third barcode;
wherein at least one of the first sequence barcode or the second sequence barcode or the third barcode is present in the first probe or the second probe or the bridge oligo, respectively;
and wherein at least one of the first probe or the second probe or bridge oligo comprises a recognition sequence for an endonuclease;
and wherein the kit of parts further comprises an oligonucleotide capable of annealing with said recognition sequence such that a recognition site for said endonuclease is obtained.

EXAMPLES

Method

1. Formation of Probe Complexes

Probe complexes contain sequences required for genomic targeting, sample indexing and constructing Illumina sequencing libraries.

Three-part probe complexes are allowed to form (as illustrated in FIG. 2), comprising:

(a) a first probe having, starting from the 5' end of the molecule, a first bridge oligo-specific sequence, and a first target specific portion at the 3' end of first probe;

(b) a second probe having, starting from the 5' end of the molecule, a second target specific portion, a second sequence barcode, and a second bridge oligo-specific sequence at the 3' end of second probe;

and (c) a bridge oligo having sequences complementary to the first bridge oligo-specific sequence and the second bridge oligo-specific sequence in the first probe and the second probe, respectively, Probe complexes are built by combining all three parts (bridge, right arm and left arm) in equimolar amounts in annealing reaction. The reaction is carried out in a thermo cycler (Annealing program in Table 1).

TABLE 1

| Step | Temperature | Time |
|---|---|---|
| 1 | +95° C. | 5 min |
| 2 | +95° C. | 1 min |
|  | −1° C./1 min, go to 2 40x |  |
| 3 | +55° C. | 10 min |
| 4 | +55° C. | 1 min |
|  | −1° C./1 min, go to 4 35x |  |
| 5 | +4° C. | hold |

2. Target Capture

Specific genomic regions containing the mutation(s) of interest are targeted. Purified DNA (for example from tissue, plasma, urine or saliva) can be used as sample or the samples can be non-purified, but only preprocessed, for example by boiling and/or centrifugation.

The probe complexes are hybridized to target regions via base sequence complementary interactions. To initiate the target capture, reaction probes and target DNA are mixed and incubated in a thermal cycler (Target capture and GapFill program in Table 2).

TABLE 2

| Step | Temperature | Time | process |
|---|---|---|---|
| 1 | +75° C. | 9 min | denaturation |
| 2 | +75° C. | 1 min | |
| | −1° C./ 1 min, go to 2 20x | | target capture |
| 3 | +55° C. | 60 min | |
| 4 | +50° C. | 10 min | GapFill |
| 5 | +45° C. | 45 min | |
| 6 | +4° C. | hold | |

3. GapFill Reaction

After target capture, probe complexes are extended and ligated by adding a combination of Phusion DNA polymerase, nucleotides and Ampligase DNA ligase and incubating 45 minutes at +45° C.

4. Rolling Circle Amplification

After extension and ligation, circular probe molecules are subjected to Rolling Circle Amplification (RCA). For RCA reaction target capture reaction is mixed with RCA reaction mix containing EquipPhi29 (Thermo Scientific) polymerase. Reaction is incubated at +42° C. for 30 min-2 hours. After RCA reaction the efficiency of reaction is analyzed by measuring the concentration of single stranded DNA (ssDNA) with Qubit fluorometer.

5. Enzymatic Digestion

RCA reaction produces a long concatemeric ssDNA molecule having multiple copies of target library. Each complete target library is separated by EcoRI restriction enzyme recognition sequence. This sequence permits sequence-specific cutting of the long concatemer via annealing with a specific oligonucleotide containing the EcoRI restriction enzyme recognition sequence and release of ready target libraries. These libraries are ready for further analysis after a simple purification step. RCA products are digested with EcoRI for 1 hour at +37° C.

6. Library Purification

After EcoRI digestion library molecules are purified by extracting them from agarose gels after electrophoresis or with size selection beads (such as Macherey Nagel Nucleo-Mag).

7. Sequencing

Purified MiSeq- or iSeq100-compatible libraries are subjected to sequence analysis using state of the art sequencing instruments. Importantly, the libraries can be converted to fit in any available sequencing platform by simple oligonucleotide modifications. Sequencing data is processed using a combination of Unix command line tools and Python and R programming languages. Briefly, the rationale for the sequence processing is to identify the probe sequences within each read, sequence the genomic area between them, and count the number of molecular barcodes associated with each genetic target.

Experiment 1.

In the first experiment the probe mix was a collection of four differentially indexed probes resulting in four replicate reactions. They targeted EML-ALK fusions. Target oligonucleotides had unique recognition sequences allowing identification of each target.

As a sample, three synthetic target oligonucleotides were mixed in logarithmically increasing concentrations. Target capture, extension and ligation reactions, rolling circle amplification and subsequent digestion with EcoRI were carried out as described above. An example of typical results is shown in FIG. 3.

Figure 4:
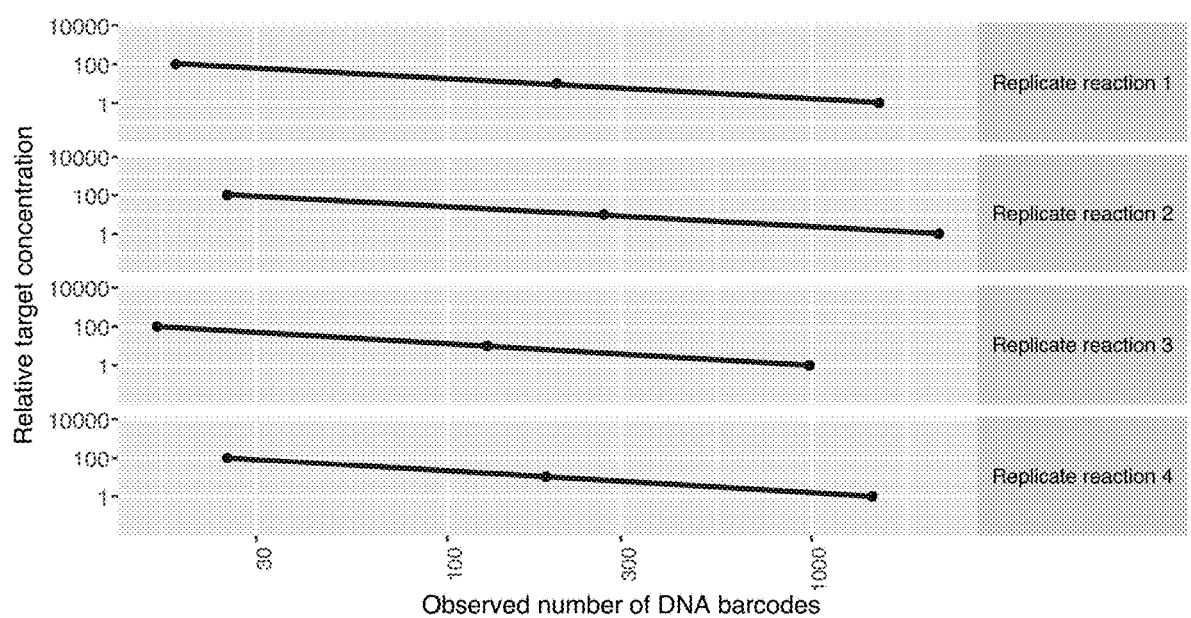
FIG. 4 illustrates the linear response of the experimental workflow to logarithmically decreasing number of genetic targets in four replicate reactions, inferred from next-generation DNA sequencing data by enumerating the molecular barcodes. Each row represents three concentrations of the target sequence. The response is linear across three orders of magnitude.

Ready libraries were sequenced with MiSeq and iSeq100 instruments and target regions were detected within the sequence data by matching the probe sequences within each read, identifying the genomic sequence area between the probe sequences and counting the molecular barcodes. The count data accurately reflected the number of spiked-in template molecules and the detected signals were highly specific to the presence of the target molecules (FIG. 4).

DETAILED DESCRIPTION OF FIGS. 1 AND 2

FIG. 1 illustrates the workflow of one embodiment of the described invention. In step 1, nucleic acids (DNA or RNA) within a sample (102) are brought into contact with a set of ligation complexes (104). The ligation complexes anneal on the target nucleic acids (106). In step 2, the target-bound ligation complexes are optionally captured from the sample material, leaving behind sample impurities (103). In step 3, the annealed ligation complexes are ligated, resulting in ligated ligation complexes. In step 4, ligated ligation complexes from multiple samples (110) are pooled together (112). In step 5, the probe sequences are amplified by rolling circle amplification using phi29 polymerase or other strand displacing polymerase, resulting in long concatemeric copies of the probes (116). In step 6, the concatemeric probe copies are optionally cleaved into monomeric units using a restriction endonuclease such as EcoRI or a homing nuclease such as I-CeuI and are optionally further amplified using PCR or emulsion PCR (117). In step 7, the amplified DNA is sequenced using next-generation DNA sequencing. In step 8, the DNA sequencing results are converted into target counts using a bioinformatic pipeline.

Figure 2A:
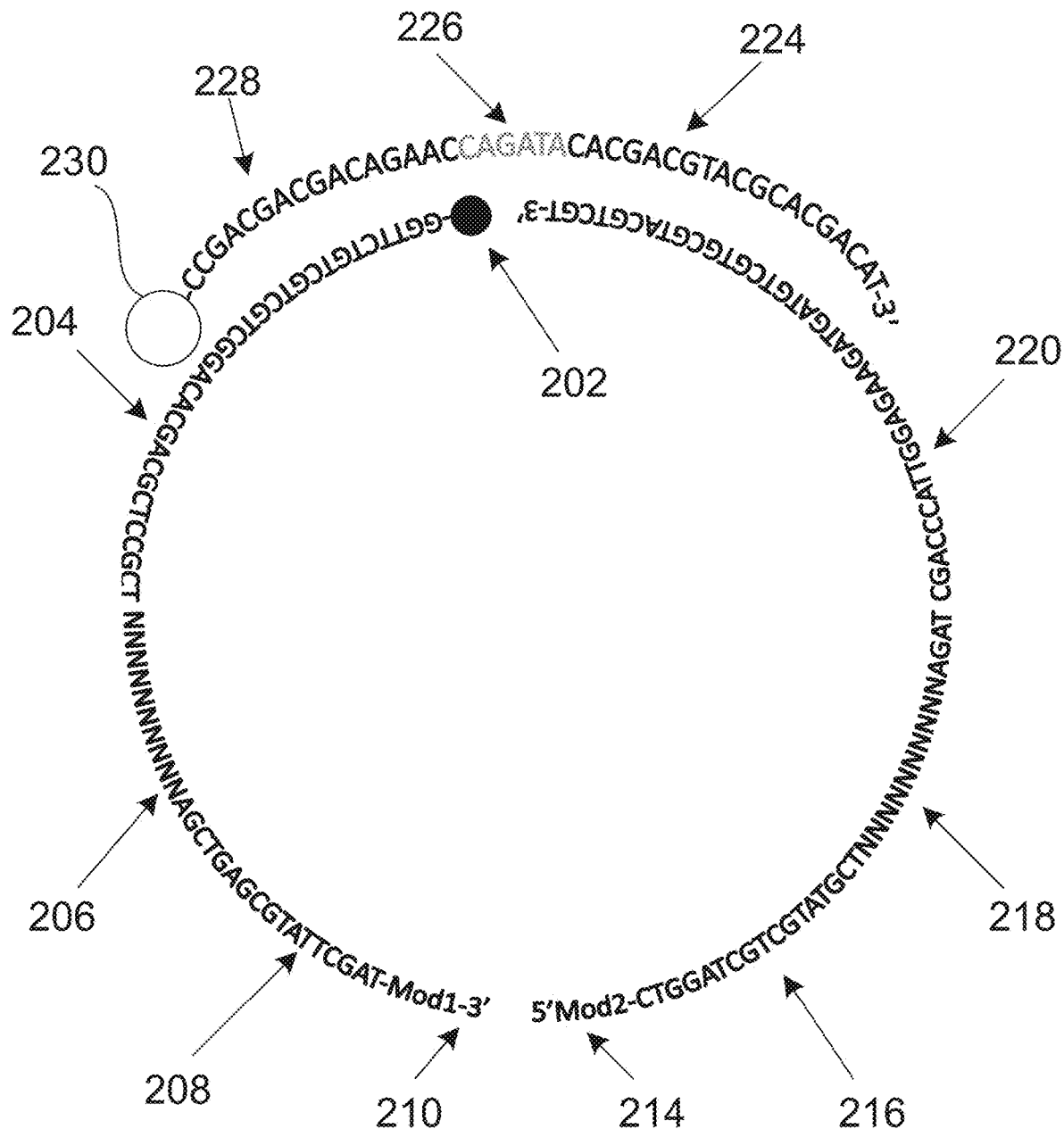
FIG. 2A illustrates a principle structure of probes triplet having a plurality of probe entities according to an embodiment herein.

FIG. 2A illustrates a principle structure of a probe triplet having a plurality of probe entities according to an embodiment herein. The plurality of probe entities include a left probe, a right probe and a bridge oligo assembled prior to sample annealing. The first base of the left probe optionally includes a phosphate moiety for enzymatic ligation or a modification that permits chemical ligation to the 5' end of the adjacent probe referred to as modification 1 (202). 15-25 bases of the left probe include a bridge binding sequence 1 (204), that further may include chemically modified bases for efficient bridge oligo binding referred as bridge site 1. The left probe further optionally includes following 10-20 bases from the 5' end including segments of random nucleotides which form the molecule-specific barcode or sample-specific barcode referred to as barcode 1 (206). The left probe further includes following 15-30 bases from the 5' end, binds to the genetic target (208). Some or all of the nucleotides of 204 or 208 may include chemical modifications that increase the affinity of the probes to the target or the bridge oligo (226). The last base of the left probe optionally includes a phosphate moiety for enzymatic ligation or a modification that permits chemical ligation to the 5' end of the adjacent probe referred to as modification 1 (210).

The first base of the right probe optionally includes a phosphate moiety for enzymatic ligation or a modification that permits chemical ligation to the 5' end of the adjacent probe referred to as modification 2 (214). The 15-30 bases from the 5' end of the right probe include a part of the right probe that binds to the genetic target (216). The following 10-20 bases from the 5' end of the right probe optionally include segments of random nucleotides which form the molecule-specific barcode or sample-specific barcode referred to as barcode 2 (218). The last 15-25 bases of the right probe include a sequence for efficient bridge oligo binding, referred as bridge sequence 2 (220). Some or all of the nucleotides of 204, 208, 216 or 220 may include chemical modifications that increase the affinity of the probes to the target or the bridge oligo.

The first 15-25 bases from the 5' end of the bridge oligo, referred as bridge sequence 3 (228), are reverse complementary to the bridge sequence 1 of the right probe (204), and optionally include chemically modified nucleotides for increased binding. The last 15-25 bases of the bridge, referred as bridge sequence 2 (224), are reverse complementary to the bridge sequence 2 sequence of the left probe (220), and optionally include chemically modified nucleotides for increased binding. The bridge sequence here includes a recognition site for a restriction endonuclease such as EcoRI or a homing endonuclease such as I-CeuI (226). The 5' end of the bridge oligo optionally includes a capture moiety (230) used for capturing the ligation complexes.

Figure 2B:
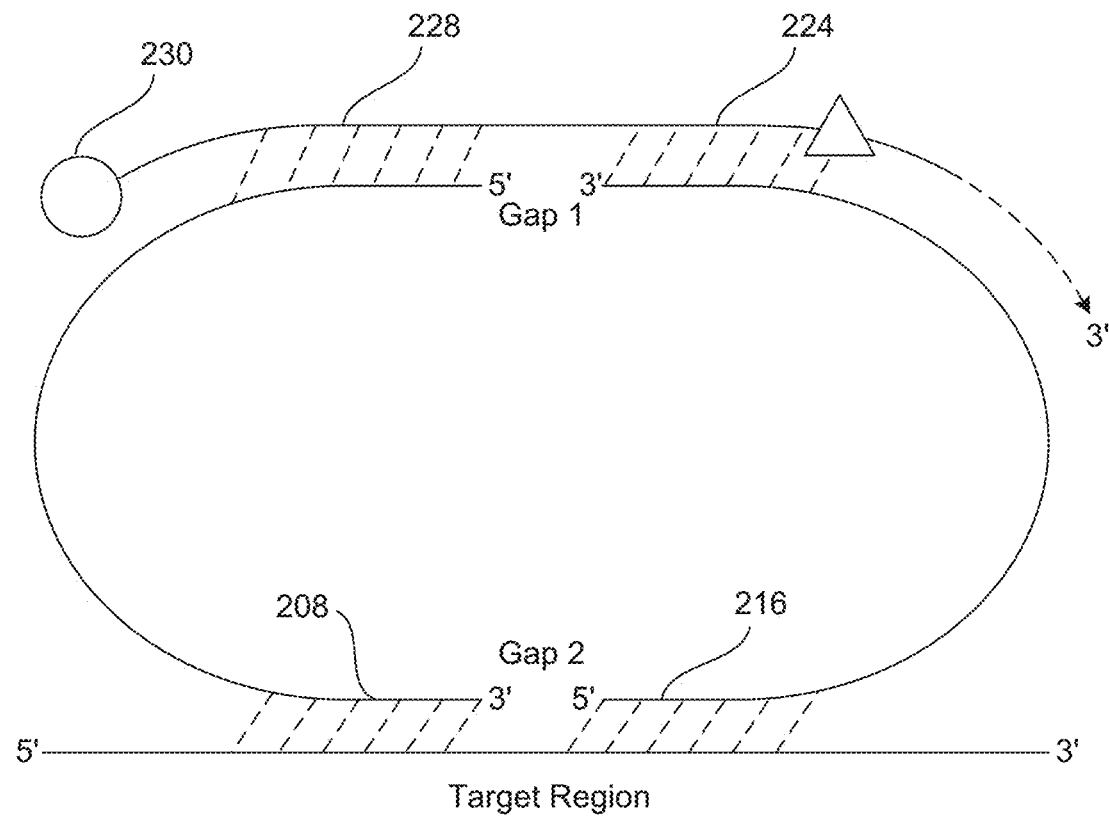
FIG. 2B illustrates the gap filling between the first probe and the second probe according to an embodiment herein.

FIG. 2B illustrates gap filling between the first probe and the second probe according to an embodiment herein. Here, the bridge oligo contains Gap1 between the bridge sequence 1 (228), and bridge sequence 2 (224). Gap2 is formed between the target binding parts of probes 1 and 2 (208 and 216). These gaps are filled by introducing a polymerase and one or more nucleotides. For this process a mixture of Stoffel fragment, Taq polymerase or Phusion polymerase, and DNA ligase such as Ampligase can be used. The polymerase adds nucleotides (a) complimentary to the universal bridge oligo sequence and (b) complimentary to the target sequence and thereby fills in the two gaps i.e. gap 1 and gap 2 between the first probe and the second probe, and the subsequent action of the DNA ligase results in ligation of the left probe and the right probe complementary to the bridge oligo and the target sequence, into a circular complex.

Figure 2C:
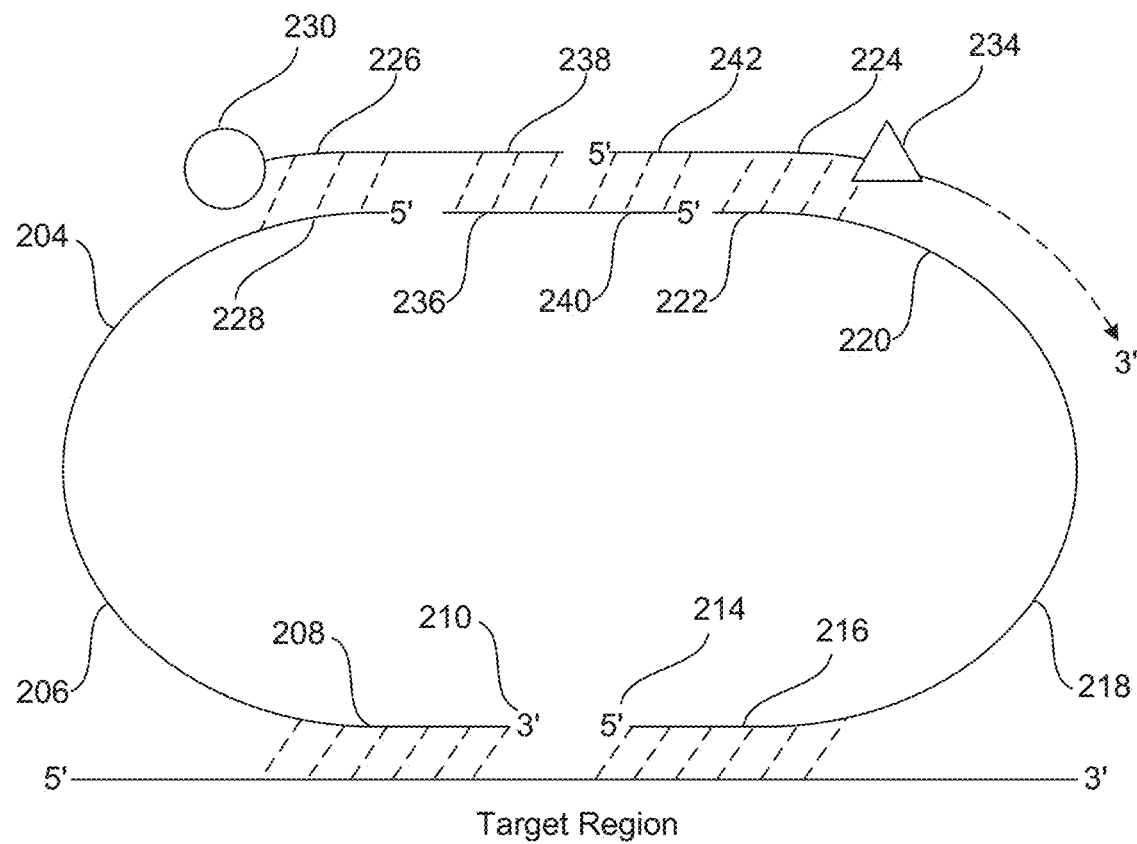
FIG. 2C illustrates the gap filling between the first probe and the second probe and the bridge complex according to an embodiment herein.

FIG. 2C illustrates a principle structure of a probe quintet having a plurality of probe entities according to an embodiment herein. The plurality of probe entities include a left probe, a right probe and an bridge consisting of three oligos. Here the probe complex contains gaps between the left probe and the second bridge (228 and 236), between the second bridge and the right probe (240 and 222), between the first and third bridge oligos (238 and 242) and between the left and right probes (208 and 216). These gaps are filled by introducing a polymerase and one or more nucleotides. For this process a mixture of Stoffel fragment, Taq polymerase or Phusion polymerase, and DNA ligase such as Ampligase can be used. The polymerase fills these gaps and the subsequent action of the DNA ligase results in ligation of the probe and bridge oligos into a circular complex.

15-25 bases of the left probe includes an bridge binding sequence 1 (228), that optionally includes chemically modified bases for efficient bridge oligo binding referred as bridge sequence 1. The left probe further optionally includes following 10-20 bases from the 5' end including universal sequence used for library indexing (204) The left probe further optionally includes following 10-20 bases from the 5' end including segments of random nucleotides which form the molecule-specific barcode or sample-specific barcode referred to as barcode 1 (206). The left probe further includes following 15-30 bases from the 5' end, binds to the genetic target (208). Some or all of the nucleotides of 228 may include chemical modifications that increase the affinity of the probes to the target or the bridge (226). The last base of the left probe optionally includes a phosphate moiety for enzymatic ligation or a modification that permits chemical ligation to the 5' end of the adjacent probe referred to as modification 1 (210).

The first base of the right probe optionally includes a phosphate moiety for enzymatic ligation or a modification that permits chemical ligation to the 5' end of the adjacent probe referred to as modification 2 (214). The 15-30 bases from the 5' end of the right probe include a part of the right probe that binds to the genetic target (216). The following 10-20 bases from the 5' end of the right probe optionally include segments of random nucleotides which form the molecule-specific barcode or sample-specific barcode referred to as barcode 2 (218). The following 10-20 bases from the 5' end of the right probe optionally include a universal sequence (220). The last 15-25 bases of the right probe, referred as bridge sequence 8 (222), are reverse complementary to the bridge sequence 7 of the third bridge oligo (224). Some or all of the nucleotides of 208, 216, 222 or 228 may include chemical modifications that increase the affinity of the probes to the target or the bridge oligo.

The first 15-25 bases from the 5' end of the first bridge oligo, referred as bridge sequence 3 (226), are reverse complementary to the bridge sequence 1 of the right probe (228), and optionally include chemically modified nucleotides for increased binding. The last 15-25 bases of the first bridge oligo, referred as bridge sequence 2 (238), are reverse complementary to the bridge sequence 4 sequence of the second bridge oligo (236), and optionally include chemically modified nucleotides for increased binding. The 5' end of the first bridge oligo optionally includes a capture moiety (230) used for capturing the ligation complexes.

The first 15-25 bases from the 5' end of the second bridge oligo, referred as bridge sequence 5 (240) are reverse complementary to the bridge sequence 6 (242) of the third bridge oligo, and optionally include chemically modified nucleotides for increased binding. The last 15-25 bases of the second bridge oligo, referred as bridge sequence 4 (236), are reverse complementary to the bridge sequence 2 sequence of the first bridge oligo (238), and optionally include chemically modified nucleotides for increased binding.

The first 15-25 bases of the third bridge oligo from the 5' end, referred as bridge sequence 6 (242), are reverse complementary to the bridge sequence 5 sequence of the second bridge oligo (240), and optionally include chemically modified nucleotides for increased binding. The last 15-25 bases of the first bridge oligo, referred as bridge sequence 7 (224), are reverse complementary to the bridge sequence 8 sequence of the right probe (222), and optionally include chemically modified nucleotides for increased binding. The 3' end of the third bridge oligo optionally includes a phosphate (or other cleavable) moiety (234) to prevent extension during gap fill.

The invention claimed is:

1. A method for the high-throughput detection of one or more target nucleotide sequence in a plurality of samples, the method comprising the steps of:
(i) providing for each target nucleotide sequence in each of the samples:
a first probe, a second probe and a bridge oligo or a plurality of oligonucleotides capable of annealing to each other to form a bridge oligo complex,
wherein the first probe comprises, starting from the 5' end of the molecule, a first bridge oligo-specific sequence, optionally a first sequence barcode, and a first target specific portion at the 3' end of first probe;
and wherein the second probe comprises, starting from the 5' end of the molecule, a second target specific portion, optionally a second sequence barcode, and a second bridge oligo-specific sequence at the 3' end of second probe;
and wherein the bridge oligo or bridge oligo complex contains sequences complementary to the first bridge oligo-specific sequence and the second bridge oligo-specific sequence in the first probe and the second probe, respectively, and optionally a third barcode;
and wherein at least one of the first sequence barcode or the second sequence barcode or the third barcode is present in the first probe or the second probe or the bridge oligo or bridge oligo complex, respectively;

and wherein at least one of the first probe or the second probe or the bridge oligo or bridge oligo complex comprises a recognition sequence for an endonuclease;

and wherein, optionally, at least one of the first probe or the second probe or the bridge oligo or plurality of oligonucleotides capable of annealing to each other to form a bridge oligo complex, comprises a first capture moiety, (ii) contacting, for each of the one or more target nucleotide sequence, the first probe and the second probe with each of the samples in a separate tube, the bridge oligo or plurality of oligonucleotides capable of annealing to each other to form a bridge oligo complex and allowing self-annealing into a plurality of ligation complexes;

(iii) contacting nucleic acids present in each of the samples to be tested for the target nucleotide sequences with the ligation complexes;

(iv) allowing the first target specific portion and the second target specific portion of the respective first probe and the second probe to hybridize to essentially adjacent sections on the target sequence, thereby forming a hybridization complex;

(v) optionally, bringing the hybridization complex in contact with a solid support comprising a second capture moiety, allowing the first capture moiety and the second capture moiety to interact such that the hybridization complexes become linked to the solid support and separating the solid-support-linked hybridization complexes from components of the samples that are not linked to the solid-support;

(vi) ligating the probes in the hybridization complexes to provide ligated ligation complexes;

(vii) optionally pooling the ligated ligation complexes from the plurality of samples;

(viii) amplifying nucleic acids from the one or more ligated ligation complexes using rolling circle amplification with a strand-displacing polymerase to form an amplified one or more single-stranded concatemeric sequence;

(ix) optionally subjecting the amplified one or more single-stranded concatemeric sequence obtained in step (viii) to annealing with a specific oligonucleotide containing a recognition sequence for an endonuclease wherein the oligonucleotide anneals with the recognition sequence specified in step (i) such that a recognition site for the endonuclease is obtained;

(x) optionally cleaving the single-stranded concatemeric sequence obtained in step (viii) or the annealed complexes obtained in step (ix) with said endonuclease to form nucleic acid fragments;

(xi) subjecting the nucleic acid fragments obtained in step (x) or concatemeric sequence obtained in step (viii) to high-throughput sequencing technology to determine the barcode sequence(s) included in the nucleic acid fragments; and (xii) identifying the presence and/or number of the target nucleotide sequence in the plurality of samples by determination of at least part of the first target specific portion and/or the second target specific portion, and/or at least part of the first barcode and/or the second barcode, and/or at least part of the third barcode, wherein steps (vi) and (vii) may be performed in any order.

2. Method according to claim 1, wherein the plurality of samples includes a blood sample, a saliva sample, a urine sample or a feces sample.

3. Method according to claim 1, wherein at least one of the first probe or the second probe or the bridge oligo or bridge oligo complex comprises a first capture moiety, wherein the method comprises step (v), and wherein the method does not comprise a step of enriching for nucleic acids prior to step (v).

4. Method according to claim 1, wherein at least one of the first probe or the second probe or the bridge oligo or bridge oligo complex comprises a first capture moiety, wherein the method comprises step (v), and wherein the first capture moiety is a biotin moiety and the second capture moiety is a streptavidin moiety or an avidin moiety.

5. Method according to claim 1, wherein at least one of the first probe or the second probe or the bridge oligo or bridge oligo complex comprises a first capture moiety, wherein the method comprises step (v), and wherein a wash step is performed between steps (v) and (vi).

6. Method according to claim 1, wherein the bridge oligo or bridge oligo complex comprises:
   (i) one to five 3' protruding bases, and/or
   (ii) 3' phosphate, and/or
   (iii) one or more phosphorothioate modifications within three positions from the 3' end.

7. Method according to claim 1, wherein the 3' end of the first probe or the 5' end of the second probe, or both, are modified to permit chemical ligation of the first probe to the second probe.

8. Method according to claim 1, wherein the bridging portion of the first probe or the second probe, or both, comprise(s) chemically modified bases to permit improved binding to the bridge oligo or bridge oligo complex.

9. Method according to claim 1, wherein the first target specific portion, the second target specific portion, the first bridge oligo-specific sequences, and/or the second bridge oligo-specific sequences, contain independently from one another, one or more chemically modified nucleotide.

10. Method according to claim 1, wherein step (viii) is performed using a phi29 polymerase or a Bst polymerase.

11. Method according to claim 1, wherein a PCR amplification is performed between step (x) and step (xi) using primers which bind to universal parts of the first and second probes, wherein said primers optionally include adapters for subsequent sequencing in step (xi).

12. Method according to claim 1, wherein genetic target enumeration is permitted by counting the number of molecular barcodes per target and per sample.

13. Method according to claim 1, wherein for two or more samples or for two or more locus/allele combinations, barcode sequences are used to genotype the sample(s) for one or more sequences and/or polymorphisms.

14. Kit of parts comprising a plurality of containers, wherein at least one container comprises one or more sets of first probe and second probe, and at least one container comprises one or more bridge oligos or plurality of oligonucleotides capable of forming a bridge oligo complex, wherein the first probe comprises, starting from the 5' end of the molecule, a first bridge oligo-specific sequence, optionally a first sequence barcode, and a first target specific portion at 3' end of first probe;

wherein the second probe comprises, starting from the 5' end of the molecule, a second target specific portion, optionally a second sequence barcode, and a second bridge oligo-specific sequence at 3' end of second probe;

wherein the bridge oligo or bridge oligo complex comprises sequences complementary to the first and second bridge oligo-specific sequences in the first and second probe, respectively, and optionally a third barcode;

wherein at least one of the first sequence barcode or the second sequence barcode or the third barcode is present in the first probe or the second probe or the bridge oligo or bridge oligo complex, respectively;

and wherein at least one of the first probe or the second probe or bridge oligo or bridge oligo complex comprises a recognition sequence for an endonuclease;

and wherein the kit of parts further comprises an oligonucleotide capable of annealing with said recognition sequence such that a recognition site for said endonuclease is obtained.

* * * * *